(12) United States Patent
Hohl et al.

(10) Patent No.: US 12,263,029 B1
(45) Date of Patent: Apr. 1, 2025

(54) COMPUTED TOMOGRAPHY SYSTEM WITH IMPROVED DATA TRANSMISSION

(71) Applicant: Siemens Healthineers AG, Forchheim (DE)

(72) Inventors: Christoph Hohl, Hahnbach (DE); Peter Michael Dueppenbecker, Herzogenaurach (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/889,906

(22) Filed: Sep. 19, 2024

(51) Int. Cl.
    *A61B 6/00*     (2024.01)
    *H04B 1/04*     (2006.01)

(52) U.S. Cl.
    CPC ............ *A61B 6/563* (2013.01); *A61B 6/4435* (2013.01); *H04B 1/0475* (2013.01)

(58) Field of Classification Search
CPC .......... A61B 3/032; A61B 6/037; A61B 6/56; A61B 6/563; A61B 6/52; A61B 6/566; A61B 6/5205; A61B 6/5211; A61B 6/5252; A61B 6/5294; G06T 11/005; G06T 11/008; G06T 2207/10072; G06T 2207/10081; G06T 2207/10112; G06T 2207/10116; G06T 2211/00; G06T 2211/40

See application file for complete search history.

(56) References Cited

U.S. PATENT DOCUMENTS 5,148,448 A    9/1992   Karam et al.
2012/0213328 A1   8/2012   Dolazza et al.
2013/0216018 A1   8/2013   Nakai et al.
2016/0174928 A1*   6/2016   Demharter ............. A61B 6/563
                                                                   370/338

FOREIGN PATENT DOCUMENTS

EP            4201336 A1    6/2023

OTHER PUBLICATIONS

Wikipedia: "Quadrature amplitude modulation", in: https://en.wikipedia.org/wiki/Quadrature_amplitude_modulation [abgerufen am Oct. 9, 2024].
Extended European Search Report for European Application No. 23199115.9 mailed Jan. 15, 2024.

* cited by examiner

*Primary Examiner* — Don K Wong
(74) *Attorney, Agent, or Firm* — Harness, Dickey & Pierce, P.L.C.

(57) ABSTRACT

A gantry of a computed tomography system is rotated relative to a fixed base body of the computed tomography system. During the rotation of the gantry, digital data is transmitted between the gantry and the base body from a data source via a modulator, a transmission channel and a demodulator to a data sink. A transmission signal generated by the modulator by modulating a data stream supplied to the modulator from the data source is pre-distorted by a pre-distortion facility. The pre-distorted transmission signal is supplied to the transmission channel. Alternatively, or in addition, a transmitted signal transmitted via the transmission channel is post-distorted by a post-distortion facility and the post-distorted signal is supplied to the demodulator. The pre-distortion rule and/or the post-distortion rule are repeatedly reset by a setting facility during the rotation of the gantry.

20 Claims, 5 Drawing Sheets

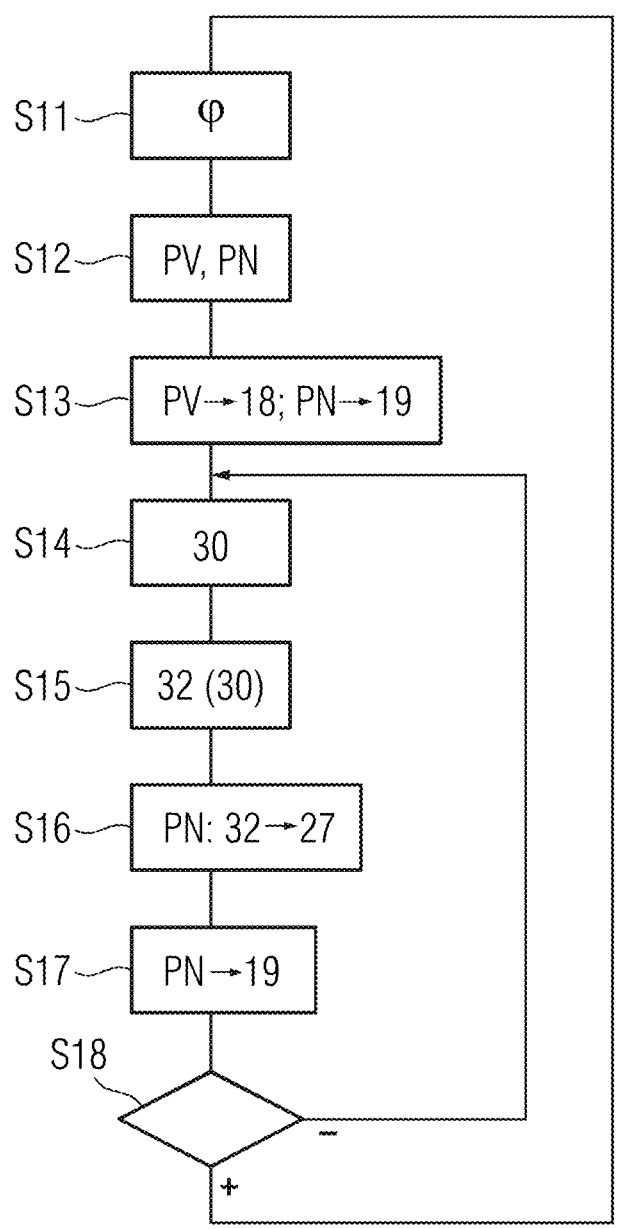

COMPUTED TOMOGRAPHY SYSTEM WITH IMPROVED DATA TRANSMISSION

CROSS-REFERENCE TO RELATED APPLICATION(S)

The present application claims priority under 35 U.S.C. § 119 to European Patent Application No. 23199115.9, filed Sep. 22, 2023, the entire contents of which is incorporated herein by reference.

FIELD

One or more embodiments of the present invention are based on an operating method for a computed tomography system,
- a gantry of the computed tomography system being rotated relative to a fixed base body of the computed tomography system, and
- digital data being transmitted from a data source via a modulator, a transmission channel and a demodulator to a data sink during the rotation of the gantry between the gantry and the base body.

One or more embodiments of the present invention are furthermore based on a computed tomography system,
- the computed tomography system comprising a fixed base body and a gantry which can be rotated relative to the fixed base body, are
- the computed tomography system comprising a data source, a modulator, a transmission channel, a demodulator and a data sink, so that digital data can be transmitted from the data source via the modulator, the transmission channel and the demodulator to the data sink during the rotation of the gantry between the gantry and the base body.

BACKGROUND

Computed tomography systems are generally known.

In a computed tomography system, an X-ray source and an X-ray detector are arranged on the gantry, the X-ray source emitting X-rays and the X-ray detector capturing the X-rays during the rotation of the gantry. Based on the images of an object of investigation (usually a person, in particular a patient) captured in this way, a three-dimensional image of the object of investigation is reconstructed.

The three-dimensional image is reconstructed by an evaluation facility which is arranged outside the gantry, for example even outside the examination room, in which the computed tomography system is arranged. The image data captured by the X-ray detector must be transmitted to the evaluation facility during the rotation of the gantry. As a rule, this takes place via a transmission channel through which the digital data from a data source (for example, a pre-evaluation facility which slightly processes the captured data of the X-ray detector) is supplied to a modem which modulates the digital data onto a carrier signal. The modulated carrier signal is supplied to another modem via a transmission channel. The other modem is arranged on the base body (fixed part). It demodulates the modulated carrier signal and feeds the received signal determined in this way to a data sink. The data source and the associated modem are in this case arranged on the gantry, the other modem and the data sink on the fixed base body. The transmission channel thus forms the bridge between the gantry and the fixed base body.

With the constant development of computed tomography systems, the volume of data to be transmitted from the data source to the data sink continues to increase. Conventional types of data transmission are increasingly reaching their limits. Attempts are therefore being made to increase the data rate at which the data is transmitted.

In the case of a computed tomography system, the carrier signal is usually modulated in a relatively simple manner, namely phase shift keying or amplitude shift keying. These modulation methods are relatively robust in the face of phase changes of the transmitted signal. The transmittable data density, on the other hand, is relatively low. It is also referred to as low spectral efficiency.

In the prior art, modulation methods are known which achieve a considerably higher data density (or have a higher spectral efficiency), in particular quadrature amplitude modulation (QAM). Purely by way of example, reference can be made to the corresponding excerpt from the German Wikipedia, accessed on Aug. 21, 2023. With regard to quadrature amplitude modulation, there are various "expansion stages", usually referred to as M-QAM, M being the number of possible values. M is generally a power of 2, usually even an even power of 2. The simplest "expansion stage" is therefore a 4-QAM. Further "expansion stages" are a 16-QAM, a 64-QAM and a 256-QAM. Even higher "expansion stages" are also known.

Quadrature amplitude modulation allows a considerably higher data rate with unchanged bandwidth of the transmission channel. However, quadrature amplitude modulation is very sensitive to phase changes of the transmitted signal because for correct demodulation, the phase of the signal generated by the modulator must be very well known on the demodulator. Even small phase shifts mean that the signal transmitted via the transmission channel cannot be demodulated correctly any longer.

It is known—see, for example, the entry already mentioned in the German Wikipedia—to distort the signal transmitted via the transmission channel via a post-distortion facility downstream of the transmission channel in accordance with a post-distortion rule and only to supply the post-distorted signal to the demodulator. The post-distortion facility is usually designed as a so-called matched filter. The transmission function of this filter is designed for the pulse shapes generated by the modulator and allows very good interference suppression.

By using quadrature amplitude modulation for data transmission between the gantry and the base body, a considerably higher data rate can be achieved than before. However, due to the fact that data transmission takes place during the rotation of the gantry, the runtime required by the transmission signal fed into the transmission channel by the modulator until it reaches the demodulator changes during data transmission. However, this also changes the phase relationship between the modulator and the demodulator. The prior art procedure of post-distorting the signal transmitted via the transmission channel in a matched filter therefore does not readily lead to the desired success.

SUMMARY

Regardless of the grammatical gender of a particular personal term (such as here, for example, the term "patient"), persons with male, female and other gender identities are always included.

An object of one or more embodiments of the present invention is to provide possibilities by which the data rate in data transmission between the gantry and the fixed base body can be increased for a certain bandwidth of the transmission channel.

At least this object is achieved by an operating method for a computed tomography system with the features of the independent claim(s). Advantageous embodiments of the operating method are the subject matter of the dependent claims.

According to an embodiment of the present invention, an operating method of the aforementioned type is designed in such a way that a transmission signal generated by the modulator by modulating a data stream fed to the modulator from the data source is pre-distorted by a pre-distortion facility (also referred to as a pre-distortion device) arranged upstream of the transmission channel in accordance with a pre-distortion rule and only the pre-distorted transmission signal is fed to the transmission channel and/or a signal transmitted via the transmission channel is post-distorted by a post-distortion facility (also referred to as a post-distortion device) arranged downstream of the transmission channel in accordance with a post-distortion rule and only the post-distorted signal is fed to the demodulator and the pre-distortion rule and/or the post-distortion rule are repeatedly reset by a setting facility (also referred to as a setting device) during the rotation of the gantry.

The pre-distortion, the post-distortion or—particularly preferably—the combination of pre-distortion and post-distortion can compensate for the distortion of the transmission signal caused by the transmission function of the transmission channel. The demodulator can thus be supplied with a signal which is virtually undistorted as a result, so that a high-quality, virtually undistorted reconstruction of the actual data signal is possible. Matched filtering is therefore carried out in a matched filter. In this respect, the procedure corresponds in approach to the procedure which is used in the prior art for quadrature amplitude modulation. However, to compensate for the changes in runtime during the rotation of the gantry, more or less continuous tracking of the pre-distortion rule and/or the post-distortion rule also takes place. As a result, the quality of the data transmission can also be maintained during the rotation of the gantry.

Preferably, the data source feeds the data stream to the modulator as a complex signal and the modulator determines the transmission signal by a quadrature amplitude modulation of a carrier signal according to the complex signal supplied. As a result, the data rate at which the data transmission takes place can be maximized. In particular, with quadrature amplitude modulation, the present invention shows its full advantages.

Preferably, the pre-distortion rule and/or the post-distortion rule are parameterizable FIR filters (FIR=Finite Impulse Response). These filters are reliable, robust and easy to parameterize, and can also be parameterized dynamically.

Preferably, the setting facility determines the pre-distortion rule and/or the post-distortion rule as a function of a respective angle of rotation of the gantry.

Preferably, the setting facility takes into account at least one time derivative of the angle of rotation in addition to the respective angle of rotation when determining the pre-distortion rule and/or the post-distortion rule.

The time derivatives can be in particular the first time derivative (i.e. the rotational speed) and/or the second time derivative (i.e. the rotational acceleration). The time derivatives are taken into account with the correct sign in particular. By taking into account the time derivatives of the angle of rotation, for example, it is possible to compensate for time delays between the detection or determination of the respective angle of rotation and the tracking of the pre-distortion rule and/or the post-distortion rule.

It is possible that the angle of rotation is measured in each case, i.e. that the tracking of the pre-distortion rule and/or the post-distortion rule is based on a measured angle of rotation. In this case too, it is possible to additionally take into account at least one time derivative of the angle of rotation when determining the pre-distortion rule and/or the post-distortion rule.

Alternatively, it is possible for the angle of rotation to be measured only at predetermined angular positions, for example only every 120°, every 180°, or even only once per complete rotation of the gantry. In this case, the angle of rotation between the predetermined angular positions is determined by the setting facility by updating the last measured angle of rotation on the basis of operating data of the gantry characterizing the rotation of the gantry, in particular the speed of rotation and/or the rotational acceleration.

Preferably, parameters for the parameterization of the pre-distortion facility and/or the post-distortion facility are stored in a lookup table in the setting facility for a multiplicity of input variables and the setting facility determines the parameters using the lookup table.

For example, the lookup table can contain the associated parameters for parameterizing the pre-distortion facility and/or the post-distortion facility for a multiplicity of grid points of the angle of rotation. If the respective angle of rotation corresponds to one of the grid points, the parameters stored for this grid point are used. If the respective angle of rotation does not correspond to any of the grid points, the parameters for the respective angle of rotation can be determined, for example, via linear interpolation of the parameters stored for the nearest grid points. Similar procedures are possible if the lookup table is not one-dimensional (utilization of the angle of rotation only), but multi-dimensional (utilization of the rotational speed in addition, etc.).

Preferably, the data stream comprises a multiplicity of data groups, the data groups each comprising a reference sequence and a useful sequence. In this case, the signal transmitted via the transmission channel comprises a reference portion and a useful portion. In this case, the reference portions are fed to the setting facility and the setting facility determines the post-distortion rule for the useful portion following the respective reference portion as a function of the respective reference portion. The background to this procedure is that the reference sequence can be known in advance to the setting facility, so that it can be known to the setting facility that the reconstructed sequence resulting after post-distortion and demodulation should correspond to the reference sequence. The setting facility can therefore track the post-distortion rule in such a way that the reconstructed sequence matches the reference sequence as closely as possible and use the correspondingly tracked post-distortion rule for the post-distortion of the useful portion of the corresponding data group. The transmitted signal may be the signal which has already been post-distorted, or the signal which has not yet been post-distorted, and also data derived from these signals.

The object is furthermore achieved by a computed tomography system with the features of claim 9. Advantageous embodiments of the computed tomography system are the subject matter of the dependent claims 10 to 15.

According to an embodiment of the present invention, a computed tomography system of the aforementioned type is designed in such a way that arranged upstream of the transmission channel there is a pre-distortion facility, by which a transmission signal generated by the modulator by modulating a data stream fed to the modulator from the data source is pre-distorted in accordance with a pre-distortion rule, so that only the pre-distorted transmission signal is fed to the transmission channel, and/or a post-distortion facility is arranged downstream of the transmission channel, by which a signal transmitted via the transmission channel is post-distorted in accordance with a post-distortion rule, so that only the post-distorted signal is fed to the demodulator, and the computed tomography system has a setting facility by which the pre-distortion rule and/or the post-distortion rule are repeatedly reset during the rotation of the gantry.

The resulting facts and advantages correspond to those of the operating method according to embodiments of the present invention.

The advantageous embodiments of the computed tomography system correspond to the advantageous embodiments of the operating method. The same applies to the resulting advantages.

BRIEF DESCRIPTION OF THE DRAWINGS

The properties, features and advantages of the present invention described above and the manner in which these are achieved will become clearer and more comprehensible in connection with the following description of the exemplary embodiments, which will be explained in more detail in connection with the drawings, in which, shown in a schematic view:

FIG. 11 shows a transmitted signal and
FIG. 12 shows a flow chart.

DETAILED DESCRIPTION

Figure 1:
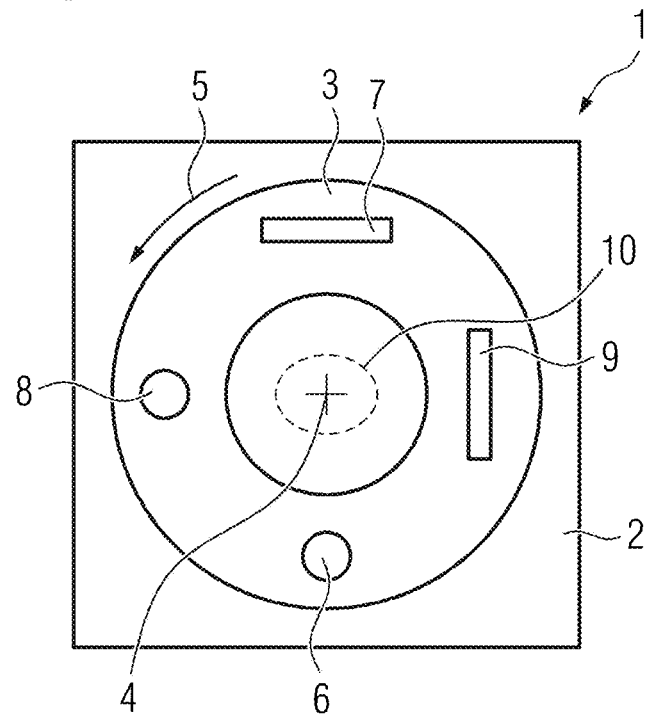
FIG. 1 shows a computed tomography system.

According to FIG. 1, a computed tomography system 1 has a fixed base body 2. A gantry 3 is rotatably mounted on the base body 2 so that the gantry 3 can be rotated relative to the base body 2 around an axis of rotation 4. The rotatability is indicated by an arrow 5 in FIG. 1. The gantry 3 carries, as is generally customary, an X-ray source 6 and an X-ray detector 7. The X-ray source 6 and the X-ray detector 7 are diametrically opposite one other with respect to the axis of rotation 4. In some cases, the gantry 3 also carries a further X-ray source 8 and a further X-ray detector 9. The further X-ray source 8 and the further X-ray detector 9 are also diametrically opposite one other with regard to the axis of rotation 4. The other X-ray source 8 and the other X-ray detector 9, if they are available, are generally arranged offset by 90° in the circumferential direction around the axis of rotation 4 as viewed with respect to the first-mentioned X-ray source 6 and the first-mentioned X-ray detector 7. During the rotation of the gantry 3 around the axis of rotation 4, the X-ray detector 7 or the X-ray detectors 7, 9 can be used to capture X-ray images of an object of investigation 10 which is arranged in the area of the axis of rotation 4.

Figure 2:
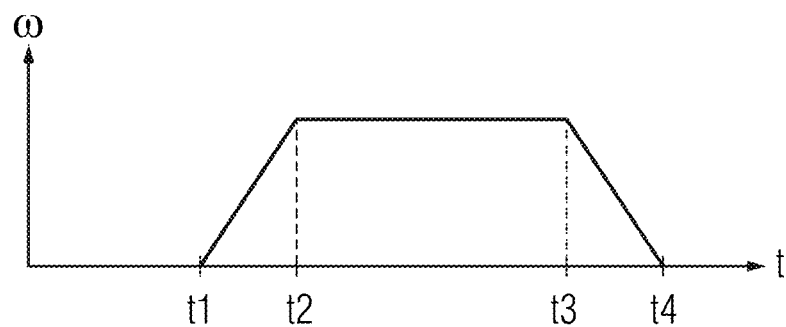
FIG. 2 shows a time diagram.

FIG. 2 shows the rotation of the gantry 3 as a function of time t. According to FIG. 2, rotation of the gantry 3 is started at a time t1 to capture the X-ray images of the object of investigation. Specifically, the gantry 3 is accelerated from the time t1 to the time t2 so that a speed of rotation ω reaches a maximum value at the time t2. The gantry 3 then rotates at the maximum speed of rotation up to a time t3 and is finally slowed down again until it comes to a standstill at a time t4.

Figure 3:
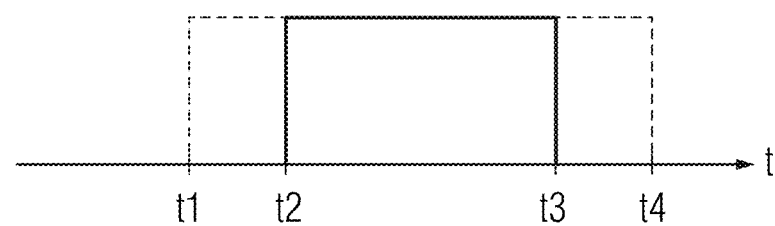
FIG. 3 shows a further time diagram.

The X-ray images are captured at least between the times t2 and t3, often even from the time t1 and up to the time t4. More or less simultaneously with the capturing of the X-ray images, the X-ray images are also transmitted according to FIG. 3 from the gantry 3 to the base body 2. FIG. 3 shows in a solid line the period of time during which at least the data transmission takes place, and in dashed lines the periods of time during which a data transmission can likewise take place. The transmitted data is of a digital nature.

Figure 4:
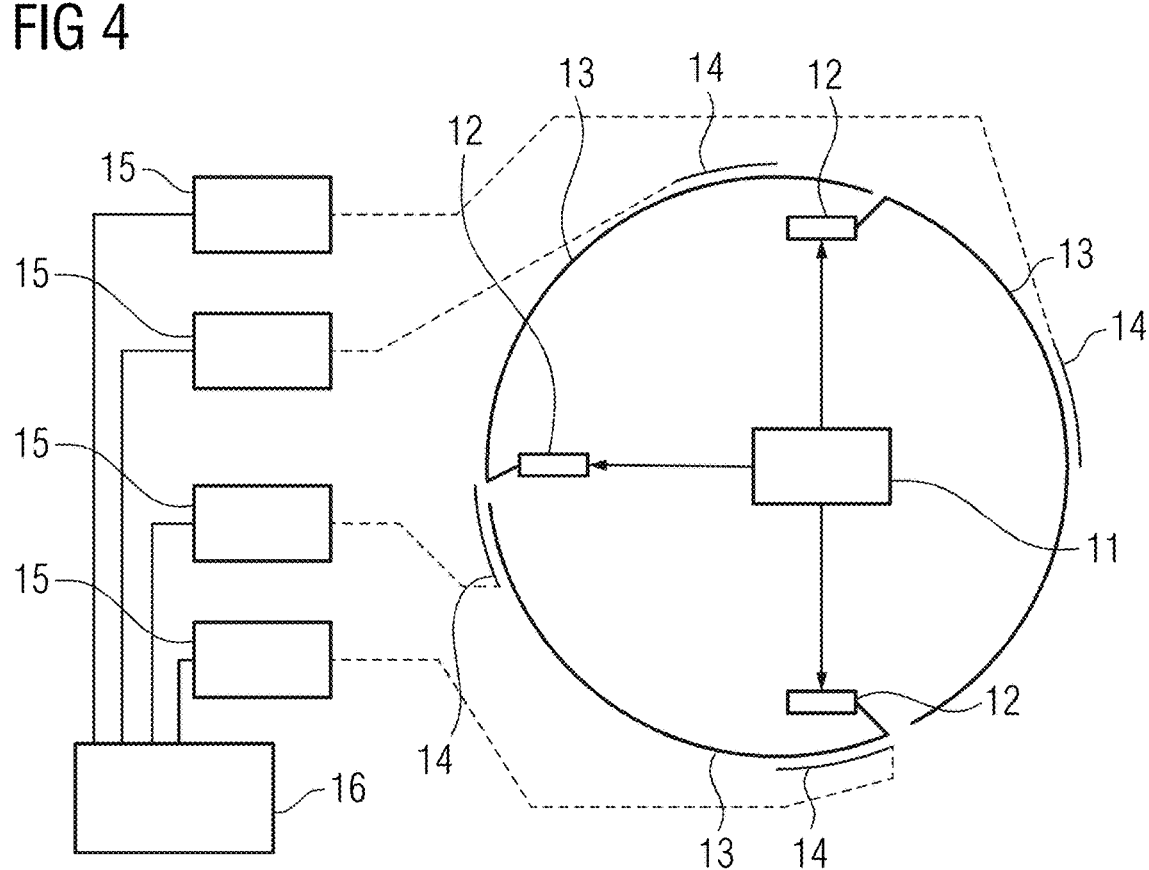
FIG. 4 shows a data transmission structure.

FIG. 4 shows in simplified form a structure for transmitting data between the gantry 3 and the base body 2.

According to FIG. 4, a data source 11 is present. The data source 11 can, for example, be a unit which receives the images from the X-ray detectors 7, 9 and processes them (slightly). The data source 11 is connected to a number of modulators 12. At a minimum, a single modulator 12 is present. In the present case, three modulators 12 are present. The modulators 12 feed transmission signals SS' (see FIG. 5) generated by them into gantry-side sections 13 of transmission channels 17 (see also FIG. 5). The sections 13 each extend over (just under) 360°/n, n being the number of modulators 12. The gantry-side sections 13 can, for example, be designed as waveguides or as dielectric conductors. Coupling elements 14 are coupled to the gantry-side sections 13 on the side of the fixed base body 2. The coupling elements 14 are generally evenly distributed around the circumference. The number of coupling elements 14 is usually greater by 1 than the number of modulators 12. From the coupling elements 14, the signals are transferred further to demodulators 15 and from there to a data sink 16. As a rule, there is a 1:1-relationship between the coupling elements 14 and the demodulators 15. The section from one of the modulators 12 to one of the demodulators 15 forms a transmission channel 17 in each case.

The data transmission was explained above in connection with the transmission of data from the gantry 3 to the base body 2. In principle, however, data could also be transmitted in the opposite direction. Furthermore, the sections 13 on the side of the solid body 2 and the coupling elements 14 on the side of the gantry 3 could also be arranged the other way round.

Hereinafter, the communication channel from the data source 11 to the data sink 16 for a single transmission path is explained again in conjunction with FIG. 5.

Figure 5:
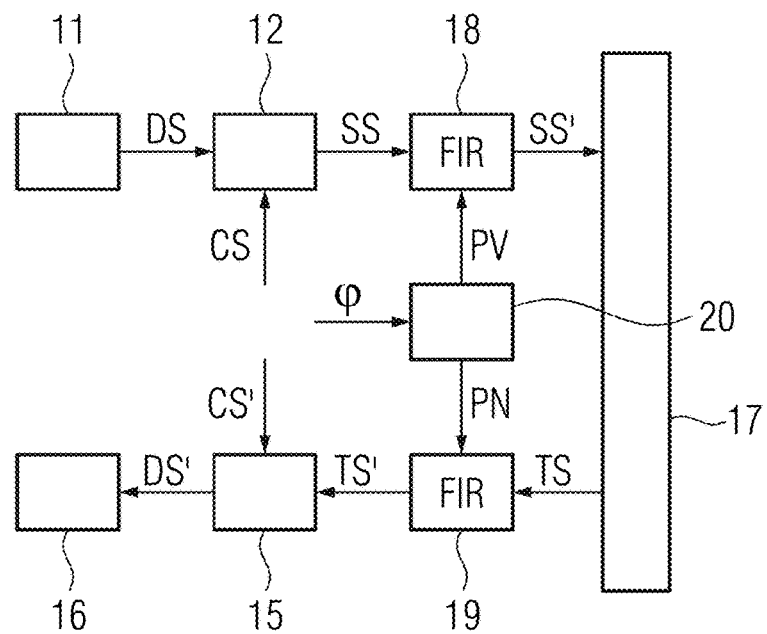
FIG. 5 shows a communication channel.

According to FIG. 5, the data is transmitted in the form of a data stream DS from the data source 11 via one of the modulators 12, the associated transmission channel 17 and one of the demodulators 15 to the data sink 16. The data transmission takes place—see FIGS. 2 and 3—during the rotation of the gantry 3. Specifically, the data source 11 transfers the data stream DS to the corresponding modulator 12. The modulator 12 modulates a carrier signal CS according to the data stream DS. The modulated carrier signal corresponds to a transmission signal SS which the modulator 12 is to feed into the transmission channel 17 from the approach. However, the transmission signal SS is first supplied to the pre-distortion facility 18. The pre-distortion facility 18 is parameterized with parameters PV. The parameterization of the pre-distortion facility 18 with the parameters PV defines a pre-distortion rule according to which the pre-distortion facility 18 performs a pre-distortion of the transmission signal SS. Only the pre-distorted transmission signal—hereinafter provided with the reference character SS' to distinguish it from the original transmission signal SS—is supplied to the transmission channel 17 and thus into the transmission channel 17. As a result, the pre-distortion facility 18 is arranged upstream of the transmission channel 17.

The signal SS' fed into the transmission channel 17 is transmitted via the transmission channel 17. This signal is referred to hereinafter as the transmitted signal and is provided with the reference character TS. After transmission, the transmitted signal TS is fed to a post-distortion facility 19. The post-distortion facility 19 is parameterized with parameters PN. The parameterization of the post-distortion facility 19 with the parameters PN defines a post-distortion rule according to which the post-distortion facility 19 performs a post-distortion of the transmitted signal TS. Only the post-distorted transmitted signal—hereinafter provided with the reference character TS' to distinguish it from the transmitted signal TS—is supplied to the demodulator 15. As a result, the post-distortion facility 19 is arranged downstream of the transmission channel 17.

The demodulator 15 demodulates the post-distorted transmitted signal TS' and thereby generates a transmitted data stream DS'. The transmitted data stream DS' is supplied to the data sink 16.

As can be seen from FIG. 4, the area of the respective section 13 at which the respective adjacent coupling element 14 couples with the respective section 13 changes continuously during the rotation of the gantry 3. As a result, the effective length of the transmission channel 17 changes continuously during the rotation of the gantry 3. Consequently, the transmission properties of the transmission channel 17 also change. In order to keep the transmission properties of the entirety of the transmission channel 17, the pre-distortion facility 18 and the post-distortion facility 19 constant or at least essentially constant, a setting facility 20 is provided. During the rotation of the gantry 3, the setting facility 20 repeatedly resets the pre-distortion rule and/or the post-distortion rule by specifying the corresponding parameters PV, PN. This is explained in more detail in conjunction with FIG. 6.

Figure 6:
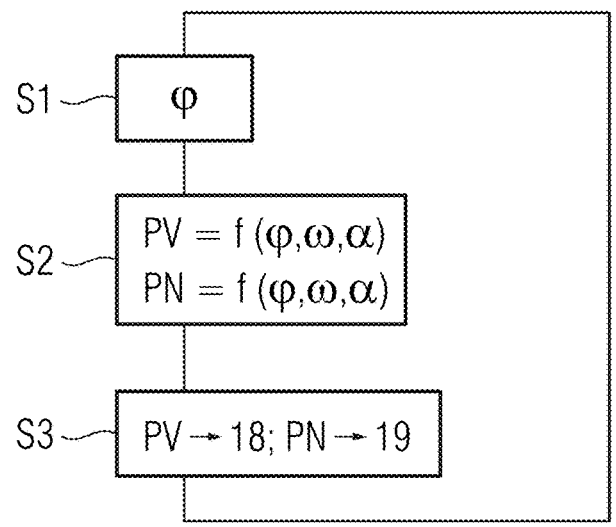
FIG. 6 shows a flow chart.

According to FIG. 6, a respective angle of rotation $\varphi$ of the gantry 3 is known to the setting facility 20 in a step S1. It is possible for the angle of rotation $\varphi$ to be detected metrologically, i.e. measured, and the corresponding measured value $\varphi$ to be fed to the setting facility 20. Alternatively, it is possible for the associated angle of rotation $\varphi$ to be measured directly or indirectly only at predetermined angular positions of the gantry 3—for example, each time a reference position is passed—and for the last measured angle of rotation $\varphi$ to be updated between the predetermined angular positions. The update can be carried out in particular on the basis of the operating data $\omega$, $\alpha$ of the gantry (3) characterizing the rotation of the gantry 3, for example, the rotational speed $\omega$ and/or the rotational acceleration $\alpha$.

In a step S2, the setting facility 20 determines the parameters PV, PN for the pre-distortion facility 18 and the post-distortion facility 19. The determination takes place as a function of the respective angle of rotation $\varphi$. If necessary, as indicated in FIG. 6, at least one time derivative of the angle of rotation $\varphi$ can also be taken into account, in particular the first time derivative, i.e. the rotational speed $\omega$, and if necessary also the second time derivative, i.e. the rotational acceleration $\alpha$.

In a step S3, the setting facility 20 outputs the parameters PV, PN determined in step S2 to the pre-distortion facility 18 and the post-distortion facility 19. This results in the resetting of the corresponding distortion rules.

The setting facility 20 then returns to step S1, so that it continuously repeats the steps S1 to S3 as a result.

The above explanations have been simplified to a certain extent. Thus, in particular, it is not necessary to execute step S1 again immediately after step S3. In many cases, it is sufficient to maintain the respective determination of the parameters PV, PN set in step S3 until a certain time has elapsed or the gantry 3 has rotated further by a certain angle.

The basic principle for determining the parameters PV, PN is explained below.

If the transmission functions of the transmission channel 17, the pre-distortion facility 18 and the post-distortion facility 19 are designated by H, U and V, then H'=UHV always applies, H' being the resulting transmission function of the pre-distortion facility 18, the transmission channel 17 and the post-distortion facility 19. Ideally, the relationship H'=I should continue to apply, I being the unit transmission function.

The transmission function H of the transmission channel 17 is variable in time due to the rotation of the gantry 3. The parameters PV, PN, with which the pre-distortion facility 18 and the post-distortion facility 19 are parameterized and which therefore determine the corresponding distortion rules and thus their transmission functions U, V, should therefore be determined at all times in such a way that the aforementioned relationship H'=I applies exactly or at least approximately.

Depending on the situation, it may be sufficient if only either the pre-distortion facility 18 is present or the post-distortion facility 19 is present or both distortion facilities 18, 19 are present, but only the parameters PV, PN of one of the two distortion facilities 18, 19 are repeatedly reset. As a rule, however, it is preferable if both the pre-distortion facility 18 and the post-distortion facility 19 are present and the parameters PV, PN of both distortion facilities 18, 19 are also repeatedly reset.

The embodiment of the pre-distortion facility 18 and the post-distortion facility 19 can be as required. In many cases, the two distortion facilities 18, 19 are designed as parameterizable FIR filters as shown in FIG. 5 or, in the case of only one distortion facility 18 or 19, the existing distortion facility 18, 19 is designed as a parameterizable FIR filter. The parameterization of the respective filter results from the respective parameters PV, PN. As a result, the pre-distortion rule and/or the post-distortion rule are preferably parameterizable FIR filters.

The embodiment of the setting facility 20 can also be as required. For example, it is possible for the setting facility 20 to determine the parameters PV, PN by way of calculation using the angle of rotation $\varphi$ (if necessary, with additional use of the rotational speed $\omega$ and/or the rotational acceleration $\alpha$). However, an embodiment as explained hereinafter in connection with FIG. 7 is considerably simpler.

Figure 7:
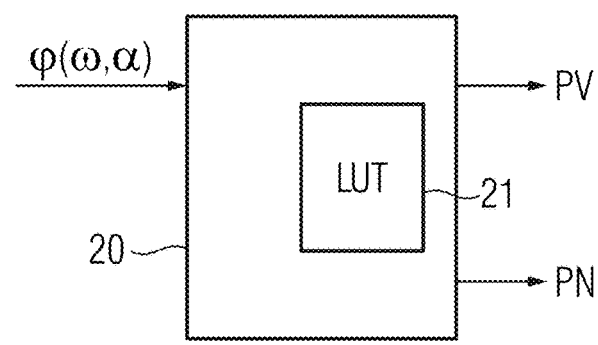
FIG. 7 shows a setting facility.

According to FIG. 7, the setting facility 20 has a lookup table 21. In the lookup table 21, parameters for the parameterization of the pre-distortion facility 18 and/or the post-distortion facility 19 are stored for a multiplicity of input variables. In the simplest case, the only input variable of the lookup table 21 is the angle of rotation φ. In this one-dimensional case, for example, the associated parameters PV, PN for the two distortion facilities 18, 19 can be stored in a grid of 2° for values from 0° to 360°. The grid dimension can of course also be finer or coarser. In the case of several input variables—for example, the angle of rotation φ and the angular velocity ω—the lookup table 21 is multidimensional. In this case, analogous embodiments apply to the angular velocity ω. The same applies if the angular acceleration α is added as an (if necessary additional) input variable to the lookup table 21. In the case of a lookup table 21, the setting facility 20 can determine the parameters PV, PN by utilizing the lookup table 21. The manner of using a lookup table 21 is generally known and therefore does not need to be explained in more detail.

Figure 8:
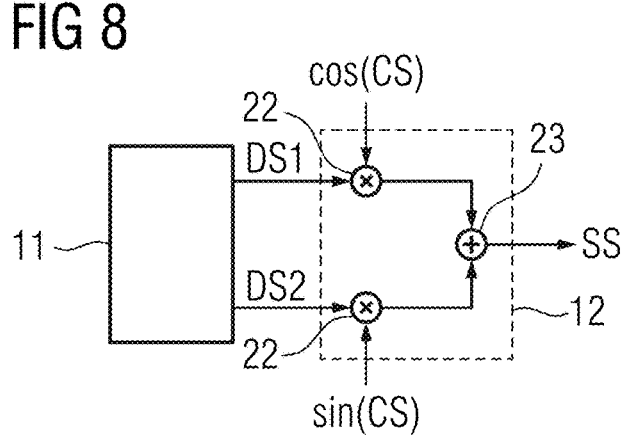
FIG. 8 shows a data source and a modulator.

The data source 11 supplies the data stream DS to the modulator 12, preferably as a complex signal, as shown in FIG. 8. The data stream DS thus comprises two partial signals DS1, DS2, which represent the real part and the imaginary part of the complex signal. In this case, the modulator 12 is designed as a quadrature amplitude modulator. It comprises two multipliers 22, to which the cosine and the sine of the carrier signal CS are fed. Furthermore, one of the two partial signals DS1, DS2 is fed to each of the two multipliers 22. The signals generated by the two multipliers 22 are fed to an adder 23, which adds the two signals to the transmission signal SS.

Figure 9:
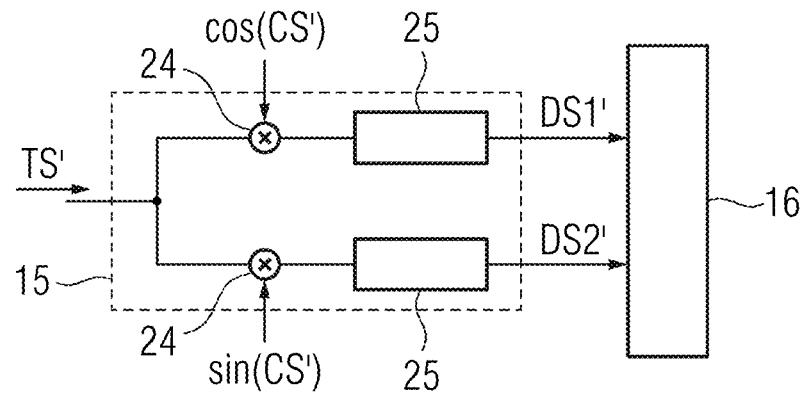
FIG. 9 shows a demodulator and a data sink.

In the case of a quadrature amplitude modulation, as shown in FIG. 9, the demodulator 15 and the data sink 16 are also designed accordingly. In particular, in this case the demodulator 15 comprises multipliers 24, to which on the one hand the post-distorted transmitted signal TS' and the cosine and the sine of a further carrier signal CS' with the same frequency as the carrier signal CS are fed. The two multipliers 24 supply the real part DS1' and the imaginary part DS2' of the demodulated signal DS' as output signals, on which a respective high-frequency component is superimposed. The respective high-frequency component is filtered out in a respective low-pass filter 25, so that the real part DS1' and the imaginary part DS2' of the demodulated signal DS' are available at the output of the respective low-pass filter 25. These two partial signals DS1', DS2' are fed to the data sink 16.

For correct demodulation, the phase of the further carrier signal CS' must match the phase of the carrier signal CS. In particular, this phase match is achieved by the two distortion facilities 18, 19 and the dynamic setting of their distortion functions.

Figure 10:
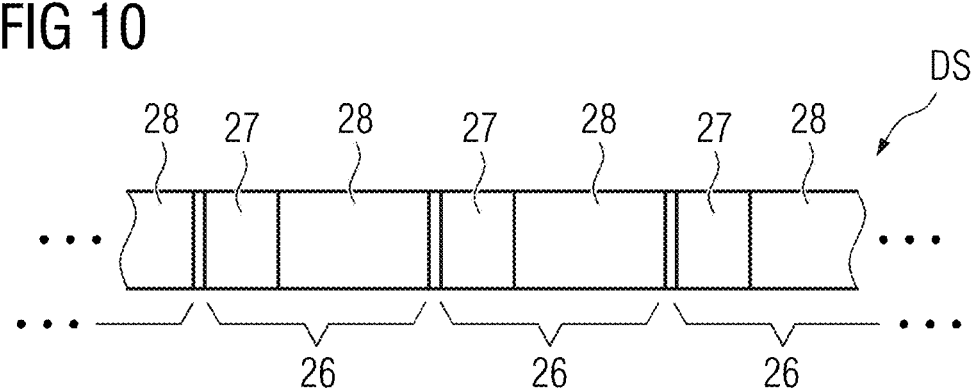
FIG. 10 shows a data stream.

According to FIG. 10, the data stream DS can comprise a multiplicity of data groups 26. This applies also and especially in the event that the data stream DS is a complex data stream. The data groups 26 each comprise a reference sequence 27 and a useful sequence 28. The reference sequence 27 is fixed in advance. Its content is therefore known not only to the data source 11, but also to the data sink 16. The useful sequence 28 contains the actual user data to be transmitted, i.e. for example, the data of the X-ray images. The data groups 26 are transferred sequentially one after the other, with the respective reference sequence 27 being transferred first and the respective useful sequence 28 being transferred only thereafter.

Figure 11:
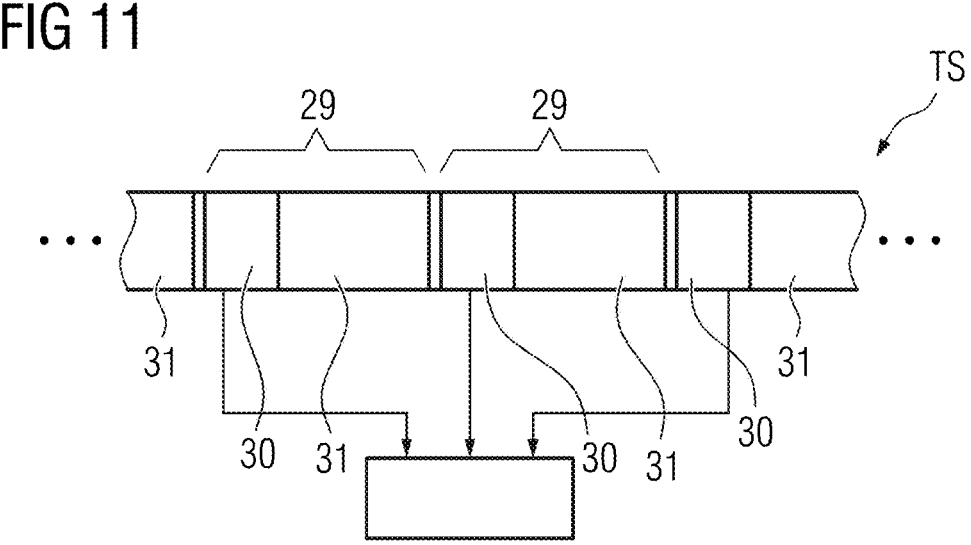

According to the sequence of data groups 26 of the data stream DS and their structure, the transmitted signal TS transmitted via the transmission channel 17 according to FIG. 11 comprises sections 29, each of which comprise a reference portion 30 and a useful portion 31. The sections 29 each correspond to a data group 26, the reference portions 30 correspond to the associated reference sequence 27 and the useful portions 31 correspond to the associated useful sequence 28. The same also applies—this is not shown separately—to the post-distorted transmitted signal TS'.

The reference portions 30 can be fed to the setting facility 20 as shown in FIG. 11. In this case, the parameterization of the post-distortion facility 19 explained above—not of the pre-distortion facility 18—can be modified as explained below in connection with FIG. 12.

According to FIG. 12, the setting facility 20 is known in a step S11 of the respective angle of rotation φ of the gantry 3. In a step S12, the setting facility 20 determines the parameters PV, PN for the pre-distortion facility 18 and the post-distortion facility 19. In a step S13, the setting facility 20 outputs the determined parameters PV, PN to the pre-distortion facility 18 and the post-distortion facility 19. The steps S11 to S13 correspond 1:1 to the steps S1 to S3 of FIG. 6. Reference is therefore made to the associated embodiments.

In a step S14, the setting facility 20 receives a respective reference portion 30. In a step S15, the setting facility 20 determines an associated reconstructed sequence 32 by demodulating the reference portion 30. In a step S16, the setting facility 20 corrects the parameters PN for the post-distortion facility 19. The correction is carried out with the aim of bringing the reconstructed sequence 32 as close as possible to the reference sequence 27, ideally bringing it into complete conformity. If necessary, the steps S15 and S16 can be executed iteratively until the parameters PN are fully optimized or at least optimized to a sufficient extent. In a step S17, the setting facility 20 outputs the corrected parameters PN to the post-distortion facility 19. As a result, the steps S14 to S17 cause the setting facility 20 to adjust the post-distortion rule depending on the respective reference portion 30. According to the post-distortion rule corrected in this way, the associated useful portion 31 is demodulated by the demodulator 15.

In a step S18, the setting facility 20 checks whether a redetermination of the parameters PV is required for the pre-distortion facility 18. The check can, for example, include a time lapse or the crossing of a certain angle range or the exceeding of a predetermined angle. If the check of the step S18 shows that a redetermination of the parameters PV is not required for the pre-distortion facility 18, the setting facility 20 returns to step S14, so that it executes steps S14 to S17 several times in succession as a result. However, if the check of step S18 shows that a redetermination of the parameters PV is required for the pre-distortion facility 18, the setting facility 20 returns to step S11, so that steps S11 to S13 are executed again.

The procedure of FIG. 12 was explained based on the transmitted signal TS, i.e. the transmitted signal not yet post-distorted. However, it is also possible to carry out the procedure of FIG. 12 with the post-distorted transmitted signal TS'. In this case, step S15 can be omitted.

In summary, the present invention thus relates to the following subject matter:

A gantry 3 of a computed tomography system is rotated relative to a fixed base body 2 of the computed tomography system. During the rotation of the gantry 3, digital data is transmitted between the gantry 3 and the base body 2 from a data source 11 via a modulator 12, a transmission channel 17 and a demodulator 15 to a data sink 16. A transmission signal SS generated by the modulator 12 by modulating a data stream DS supplied to the modulator 12 from the data source 11 is pre-distorted according to a pre-distortion rule by a pre-distortion facility 18 arranged upstream of the transmission channel 17. Only the pre-distorted transmission signal SS' is fed to the transmission channel 17. Alternatively or additionally, a transmitted signal TS transmitted via the transmission channel 17 is post-distorted by a post-distortion facility 19 downstream of the transmission channel 17 in accordance with a post-distortion rule and only the post-distorted signal TS' is fed to the demodulator 15. The pre-distortion rule and/or the post-distortion rule are repeatedly reset by a setting facility 20 during the rotation of the gantry 3.

The present invention has many advantages. In particular, comparatively simple and yet robust data transmission is created, by which high transmission rates in the range of several gigabits per second can be achieved.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been illustrated and described in more detail by the preferred exemplary embodiment, the present invention is not limited by the disclosed examples and other variations may be derived therefrom by a person skilled in the art without departing from the scope of the present invention.

What is claimed is:

1. An operating method for a computed tomography system, the operating method comprising:
    rotating a gantry of the computed tomography system relative to a fixed base body of the computed tomography system;
    transmitting, during rotation of the gantry, between the gantry and the fixed base body, digital data from a data source to a data sink via a modulator, a transmission channel and a demodulator;
    at least one of
        pre-distorting a transmission signal via a pre-distortion facility arranged upstream of the transmission channel in accordance with a pre-distortion rule and only supplying the pre-distorted transmission signal to the transmission channel, the transmission signal generated by the modulator by modulating a data stream supplied to the modulator from the data source, or
        post-distorting a transmitted signal transmitted via the transmission channel via a post-distortion facility arranged downstream of the transmission channel in accordance with a post-distortion rule and only supplying the post-distorted signal to the demodulator; and
    repeatedly resetting, by a setting facility, at least one of the pre-distortion rule or the post-distortion rule during the rotation of the gantry.

2. The operating method as claimed in claim 1, wherein
    the data source supplies the data stream to the modulator as a complex signal, and
    the modulator determines the transmission signal by a quadrature amplitude modulation of a carrier signal in accordance with the complex signal.

3. The operating method as claimed in claim 1, wherein at least one of the pre-distortion rule or the post-distortion rule are parameterizable FIR filters.

4. The operating method as claimed in claim 1, wherein the setting facility determines at least one of the pre-distortion rule or the post-distortion rule as a function of a respective angle of rotation of the gantry.

5. The operating method as claimed in claim 4, wherein the setting facility takes into account at least one time derivative of the respective angle of rotation in addition to the respective angle of rotation when determining the at least one of the pre-distortion rule or the post-distortion rule.

6. The operating method as claimed in claim 4, wherein the respective angle of rotation is measured in each case or the respective angle of rotation is measured only at predetermined angular positions and is determined between the predetermined angular positions by updating a last measured angle of rotation on the basis of operating data of the gantry characterizing the rotation of the gantry, wherein the operating data of the gantry characterizes at least one of rotational speed or rotational acceleration of the gantry.

7. The operating method as claimed in claim 1, wherein
    parameters for a parameterization of at least one of the pre-distortion facility or the post-distortion facility are stored in a lookup table in the setting facility for a multiplicity of input variables, and
    the setting facility determines the parameters using the lookup table.

8. The operating method as claimed in claim 1, wherein
    the data stream includes a multiplicity of data groups,
    each of the multiplicity of data groups includes a reference sequence and a useful sequence, so that the transmitted signal transmitted via the transmission channel includes a reference portion and a useful portion,
    the reference portion is supplied to the setting facility, and
    the setting facility tracks the post-distortion rule for the useful portion following a respective reference portion as a function of the respective reference portion.

9. A computed tomography system, comprising:
    a fixed base body;
    a gantry configured to rotate relative to the fixed base body;
    a data source;
    a modulator;
    a transmission channel;
    a demodulator; and
    a data sink;
    wherein during rotation of the gantry between the gantry and the fixed base body, the data source is configured to transmit digital data to the data sink via the modulator, the transmission channel and the demodulator;
    wherein at least one of
        a pre-distortion facility is arranged upstream of the transmission channel, wherein, via the pre-distortion facility, a transmission signal is pre-distorted in accordance with a pre-distortion rule such that only the pre-distorted transmission signal is supplied to the transmission channel, the transmission signal being generated by the modulator by modulating a data stream supplied to the modulator from the data source, or a post-distortion facility is arranged downstream of the transmission channel, wherein the post-distortion facility is configured to post-distort a transmitted signal transmitted via the transmission channel in accordance with a post-distortion rule, such that only the post-distorted signal is supplied to the demodulator; and wherein the computed tomography system includes a setting facility by which at least one of the pre-distortion rule or the post-distortion rule are repeatedly reset during the rotation of the gantry.

10. The computed tomography system as claimed in claim 9, wherein the modulator is a quadrature amplitude modulator configured to determine the transmission signal on the basis of a complex signal supplied to the modulator from the data source in accordance with quadrature amplitude modulation.

11. The computed tomography system as claimed in claim 9, wherein at least one of the pre-distortion facility or the post-distortion facility are configured as parameterizable FIR filters.

12. The computed tomography system as claimed in claim 9, wherein the setting facility is configured to determine at least one of the pre-distortion rule or the post-distortion rule as a function of a respective angle of rotation of the gantry.

13. The computed tomography system as claimed in claim 12, wherein the setting facility is configured to take into account at least one time derivative of an angle of rotation in addition to the angle of rotation when determining the at least one of the pre-distortion rule or the post-distortion rule.

14. The computed tomography system as claimed in claim 9, wherein the setting facility has a lookup table in which parameters for parameterizing at least one of the pre-distortion facility or the post-distortion facility are stored for a multiplicity of input variables in each case, and the setting facility is configured to determine the parameters using the lookup table.

15. The computed tomography system as claimed in claim 9, wherein the data stream includes a multiplicity of data groups, each of the multiplicity of data groups includes a reference sequence and a useful sequence, such that the transmitted signal transmitted via the transmission channel includes a reference portion and a useful portion, the reference portion is supplied to the setting facility, and the setting facility tracks the post-distortion rule for the useful portion following a respective reference portion as a function of the respective reference portion.

16. The operating method as claimed in claim 2, wherein the setting facility determines at least one of the pre-distortion rule or the post-distortion rule as a function of a respective angle of rotation of the gantry.

17. The operating method as claimed in claim 2, wherein the data stream includes a multiplicity of data groups, each of the multiplicity of data groups includes a reference sequence and a useful sequence, so that the transmitted signal transmitted via the transmission channel includes a reference portion and a useful portion, the reference portion is supplied to the setting facility, and the setting facility tracks the post-distortion rule for the useful portion following a respective reference portion as a function of the respective reference portion.

18. The computed tomography system as claimed in claim 10, the setting facility is configured to determine at least one of the pre-distortion rule or the post-distortion rule as a function of a respective angle of rotation of the gantry.

19. The computed tomography system as claimed in claim 18, wherein the data stream includes a multiplicity of data groups, each of the multiplicity of data groups includes a reference sequence and a useful sequence, so that the transmitted signal transmitted via the transmission channel includes a reference portion and a useful portion, the reference portion is supplied to the setting facility, and the setting facility tracks the post-distortion rule for the useful portion following a respective reference portion as a function of the respective reference portion.

20. The computed tomography system as claimed in claim 10, wherein the data stream includes a multiplicity of data groups, each of the multiplicity of data groups includes a reference sequence and a useful sequence, so that the transmitted signal transmitted via the transmission channel includes a reference portion and a useful portion, the reference portion is supplied to the setting facility, and the setting facility tracks the post-distortion rule for the useful portion following a respective reference portion as a function of the respective reference portion.

\* \* \* \* \*